United States Patent
Wulf

(10) Patent No.: US 6,319,194 B1
(45) Date of Patent: Nov. 20, 2001

(54) PENIS ERECTION STABILIZER USING TWO CONNECTED FLEXIBLE LATEX RINGS

(76) Inventor: Lynn G. Wulf, 1470 S. Quebec Way, Unit 270, Denver, CO (US) 80231-2664

( * ) Notice: Subject to any disclaimer, the term of this patent is extended or adjusted under 35 U.S.C. 154(b) by 0 days.

(21) Appl. No.: 09/494,460

(22) Filed: Jan. 31, 2000

(51) Int. Cl.$^7$ ........................................... A61F 5/00
(52) U.S. Cl. ................................................ 600/41
(58) Field of Search .................... 600/38, 39, 41

(56) References Cited

U.S. PATENT DOCUMENTS

| | | | |
|---|---|---|---|
| 4,568,340 | * | 2/1986 | Giacalone ............................. 604/353 |
| 5,622,186 | * | 4/1997 | Schwartz ............................. 600/38 X |
| 5,694,948 | * | 12/1997 | Jahangiri-Famenini ............. 128/842 |
| 5,951,460 | * | 9/1999 | Vollrath .................................. 600/38 |
| 5,964,695 | * | 10/1999 | Vollrath et al. ........................ 600/38 |

* cited by examiner

Primary Examiner—John P. Lacyk
Assistant Examiner—Joseph A. Cadugan

(74) Attorney, Agent, or Firm—Edwin H. Crabtree; Ramon L. Pizarro; Donald W. Margolis

(57) ABSTRACT

A penis erection stabilizer adapted for mounting on the base of a male penis. The penis stabilizer is designed to apply harmless pressure around the circumference of the penis base. The stabilizer helps trap a blood supply in the penis for creating and maintaining a bigger, longer lasting natural erection during sexual intercourse. The stabilizer includes an outer ring, a concentric smaller inner ring and a latex sheath. The latex sheath connects the two rings. The outer ring and smaller inner ring are also made of latex. One end of the sheath is attached to an inner circumference of the outer ring. An opposite end of the sheath is attached to an inner circumference of the inner ring. In operation, the user of the stabilizer removes the item from an air tight package. The outer and inner ring are then stretched over the head of the penis and along the length of the penis. The smaller inner ring is then placed next to the base of the penis and next to the torso with the outer ring disposed around the inner ring. The inner ring with added pressure from the outer ring provide a necessary pressure to contain the blood supply in the penis, thus helping insure a natural erection. Also, the inner ring can be unrolled from a portion of the sheath for placing the inner ring next to the upper ring.

10 Claims, 3 Drawing Sheets

PENIS ERECTION STABILIZER USING TWO CONNECTED FLEXIBLE LATEX RINGS

BACKGROUND OF THE INVENTION (a) Field of the Invention

This invention relates to a sex aid device and more particularly, but not by way of limitation, to a penis erection stabilizer for mounting on the base of a male penis for helping maintain a harder erection for a longer period of time.

(b) Discussion of Prior Art 100 years ago, G. R. Phillips, M.D. wrote the following in the *St.Louis Medical Era*, 1895–1896: "With rare exceptions, it is the evident intent of nature that every adult male be accorded the pleasure, satisfaction and the power of performing the sexual act. When a condition exists that strips one of this right, be the condition a real or a fancied ill, we have resulting impotence. To acquire an erection is essential, to maintain the same for a time sufficient for the completion of the sexual act is equally so, that one may be potent." All fields of medical science advanced during the Victorian Age, and the study of the male penis became scientific. Early urologists laid down rules in an exact science for performing observations and testing the soundness of the their conclusions. Their conclusions were that impotency does exist.

Now more than 100 years later and with all the research done on this subject, millions of men around the world still suffer impotence at some time in their lives. However, in the past decade there have been critical advances in the treatment of impotence and especially in the past year when more awareness about the word "penis" came into existence and this word emerged into mainstream conversations because of the President Clinton and Moncia Lewinski sexual encounters and the release of a new prescription drug having a brand name of "VIAGRA". Impotence is now seen by most therapists as a physiological rather than a psychological problem. The word "impotence" itself, like frigidity for women, is considered suspect in many circles. Now, the more politically correct term is "erectile dysfunction" or ED.

Inspired by a 1992 National Institutes of Health Conference or NIH and a landmark study of the problem, the diagnosis has been defined more broadly, from the rather strict criterion of the inability to get an erection to the somewhat subjective criterion of the inability to maintain an erection adequate for satisfactory sexual performance or satisfying your sexual partner. This has led to a tripling of the number of men estimated to be impotent. Some 30 million in America alone suffer from impotence according to the NIH.

Erectile dysfunction associates with age: Half of the 30 million men are thought to be under the age of 65; about 1 in 3 of the men are in an age range of 40 to 65; and 3 in 4 of the men over the age of 63 suffer from some degree of ED reports the New England Research Institute or NERI. Nevertheless in any age group, erectile dysfunction can be caused by stress, hormone imbalances, spinal injury, alcoholism, drugs, diuretics, steroids, high blood pressure medication, depression, fear, inhibitions, diabetes and surgery for prostate cancer. Also, it was reported on 60 Minutes, CBS TV, Nov. 8, 1998 that a side effect from cigarette smoking will be diminished sexual desire. Further, urologists say smoking can diminish sexual erections by reducing the blood flow in the penis, just as it can block and clog blood vessels to the heart. Still further, Dr. Irwin Golstein, M.D., Boston University Medical Center, reports that bicycle riding has made some 100,000 men impotent.

In U.S. Pat. No. 594,815 to Taggart, U.S. Pat. No. 1,511,572 to Marshall, U.S. Pat. No. 2,018,328 to Smith, U.S. Pat. No. 2,581,114 to Larson, U.S. Pat. No. 2,818,855 to Miller, U.S. Pat. No. 3,401,687 to Hood, U.S. Pat. No. 3,621,840 to Macchioni, U.S. Pat. No. 3,705,580 to Gauthier, U.S. Pat. No. 4,224,933 to Reiling, U.S. Pat. No. 4,529,980 to Chaney, U.S. Pat. No. 4,723,538 to Stewart et al. and U.S. Pat. No. 5,282,795 to Finney different types of male erection devices are described. The devices include elastic rings, surgical devices and sexual aids for constricting blood flow from the male penis and helping with impotency.

The design characteristic differentiating the invention described herein from the prior art is the use of two (2) connected rings each having separate responsibilites incorporated into a single unit. The two rings, a smaller diameter inner ring and a larger outer ring, are both on the same latex plastic device, they are both on a horizontal plane directly in-line or directly over one another and they are concentric circles. Also, the rings are flexible allowing the entry of the body/shaft of the penis through the two rings of latex. The two connected different diameters create two different size ring openings for body flow in and out of the shaft of the penis.

Heretofore, all prior art penis rings have had only one ring regardless of the ring's structure and type of material used. With the use of only one ring, it is impossible to create Biohematohydraulics, or more literally, body blood liquid hydraulic pressure and force within the shaft of the penis erectile tissue.

The subject invention provides a novel and unique erection stabilizer which is different in structure and function when compared to other prior art penis rings and sexual aids used in maintaining an erection.

SUMMARY OF THE INVENTION

The subject inventor has addressed and helps solve a biological phenomenon of maintaining an erect penis for potency and for satisfactory sexual performance. The subject invention is called "Your Erection Stabilizer" or "YES". The use of YES is based on a principal called "Biohematohydraulics", a term adopted by the inventor. Using YES maintains an erect penis, producing and prolonging a tumescent (swelling as a response to sexual stimulation) along with a fuller, a harder and a longer lasting erect penis for a longer period of time.

When wearing YES, a bigger in length and diameter erect penis can be sustained. The use of YES requires no drugs or pills, needle injections in the side of the penis and the use of a clumsy vacuum pump.

Another YES value is the longing and need for more love-making and more sexual activity in marriages. Edward Lauman, Professor of Sociology at the University of Chicago, completed a study in 1992 that showed an amazing 45 percent of men and 55 percent of women ages 18 to 59 surveyed reported they suffered some form of sexual dysfunction over just the previous twelve months. Other marriage counselors say women like foreplay the most. Wearing YES, a male, at any age, can maintain an erect penis producing a profound improvement in providing longer and more pleasurable hours of foreplay. Also, wearing YES, a male has a significantly improved penis erection satisfying himself and his lover for a longer duration. Further, YES allows men to maintain an erection even after an orgasm providing more afterplay sexual activity and even for multiple orgasms. YES will create and provide more positive and essential emotions in a marriage, thereby helping save marriages.

In view of the foregoing, it is a primary object of the subject invention to provide a penis erection stabilizer or your erection stabilizer, YES, adapted for mounting on the base of a male penis. The penis stabilizer is designed to apply harmless pressure around the circumference of the base of the penis. The stabilizer helps trap a blood supply inside the penis.

Another object of the invention is the erection stabilizer is used for creating and maintaining a bigger, longer lasting natural erection during sexual intercourse.

Still another object of the invention is the erection stabilizer is made of stretchable latex rubber and is easy to apply over the head of the penis and positioned next to the base of the penis prior to sexual intercourse. The stabilizer includes a pair of connected concentric rings which can be adjusted on the base of the penis for applying pressure therearound and holding the blood supply in the penis for a firmer erection.

Yet another object of YES is its simplicity, ease of use, discretion and functionality of solving erectile dysfunction for any male at any age. YES is safe, small, inexpensive and easy to store and carry.

The stabilizer includes an outer ring, a concentric smaller inner ring and a latex sheath connecting the two rings. The outer ring and smaller inner ring are also made of latex. One end of the sheath is attached to an inner circumference of the outer ring. An opposite end of the sheath is attached to an inner circumference of the inner ring.

In operation, the user of the stabilizer removes the item from an air tight package. The outer and inner concentric rings are then stretched over the head of the penis and moved along the length or shaft of the penis. The smaller inner ring is then placed next to the base of the penis next to the torso with the outer ring disposed over and around the inner ring. The inner ring with added pressure from the outer ring provides a necessary pressure to contain the blood supply in the penis, thus helping insure a natural erection. Also, the inner ring can be unrolled from a portion of the sheath for placing the inner ring beside the upper ring. At this time, both the inner circumference of the outer ring and the inner circumference of the connected inner ring are disposed around the base of the penis independent of each other and free standing.

The two rings may have different diameters as long as the inner ring is smaller in diameter than the outer ring. The purpose being for the two connected rings to create Biohematohydraulics. For example, different size combinations, different ratios of the diameter of the inner and outer ring could be utilized for different sizes of the adult male penis. Also, YES can be used on stud farms when breeding different types of animals.

These and other objects of the present invention will become apparent to those familiar with the different types of sex aid devices designed to help increase male potency from the following detailed description, showing novel connectivity construction, combination, and elements as herein described, and more particularly defined by the claims, it being understood that changes in the embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments of the present invention according to the best modes presently devised for the practical application of the principles thereof, and in which.

DESCRIPTION OF THE PREFERRED EMBODIMENTS

Figure 1:
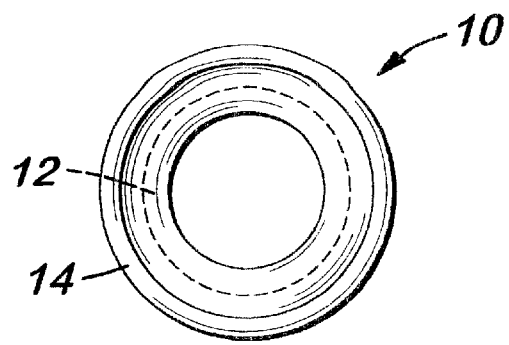
FIG. 1 is a front view of the erection stabilizer with a inner ring disposed in front of a larger outer ring. The stabilizer is shown in a relaxed state prior to being stretched over a head of a penis.
Figure 2:
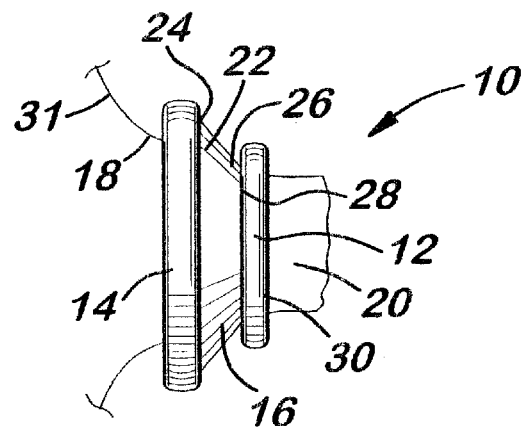
FIG. 2 is a side view of the stabilizer illustrating one end of a sheath attached to an inner circumference of the outer ring. An opposite end of the sheath is attached to an inner circumference of the inner ring. The inner ring is designed to roll up on the sheath for placing an outer circumference of the inner ring next to the inner circumference of the outer ring. The stabilizer is shown received around the base of the penis.

In FIG. 1, a front view of the erection stabilizer and referred to above as "YES". The stabilizer or YES is shown having a general reference numeral 10. Broadly, the erection stabilizer 10 includes a smaller inner ring 12, a larger outer ring 14 and a sheath 16 connecting the two rings. The sheath 16 is shown in FIG. 2. The rings 12 and 14 and the sheath 16 are made of a stretchable latex rubber for receipt around a base 18 of a male penis 20. The penis 20 is shown in FIGS. 2–7. The smaller inner ring 12 typically has an inner diameter of approximately ½ inch in a relaxed state and is concentric with the larger outer ring 14. The larger outer ring 14 has a larger inner diameter in a range of ¾ to ⅞ inches in a relaxed state.

The YES two connected rings 12 and 14 are disposed on a horizontal plane directly in-line with each other or may be positioned directly over one another. Also, the rings are concentric circles and are sufficiently flexible to allow the rings to be slipped over the head of the penis and along the length of the shaft of the penis.

In FIG. 2, a side view of the stabilizer 10 os shown illustrating one end 22 of a sheath 16 attached to an inner circumference 24 of the outer ring 14. An opposite end 26 of the sheath 16 is attached to an inner circumference 28 of the inner ring 12. The inner ring 12 is designed to roll up on a portion of the opposite end 26 of the sheath 16 for placing an outer circumference 30 of the inner ring 12 next to the inner circumference 24 of the outer ring 14. The outer ring 14 is also designed to roll up on a portion of the end 22 of the sheath 16. In this drawing, the inner ring 12 has been unrolled from a portion of the sheath 16. The erection stabilizer 10 is shown mounted on the base of the penis 20 and disposed next to a torso.

Figure 3:
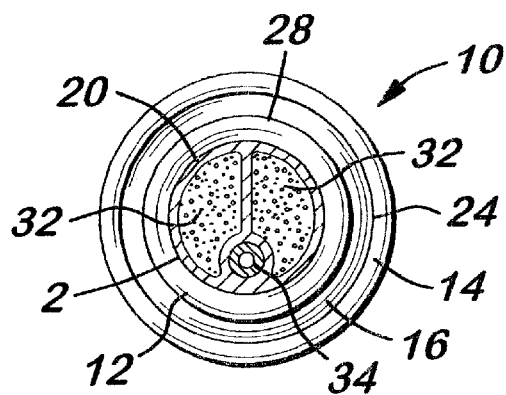
FIG. 3 is a front view of the erection stabilizer similar to the view of the stabilizer shown in FIG. 1. In this drawing a cross section of the penis is shown with the inner ring disposed around the circumference of the penis.

In FIG. 3, a front view of the erection stabilizer 10 is shown and similar to the view of the stabilizer shown in FIG. 1. In this drawing a cross section of the male penis 20 is shown with the inner circumference 28 of the inner ring 12 disposed around the circumference of the penis 20. The penis 20 as shown includes the soft spongy corpora cavernosa 32 which receives the blood supply therein for creating an erection during sexual intercourse. Also, a urethra 34 is shown in a lower portion of the penis 20.

Figure 4:
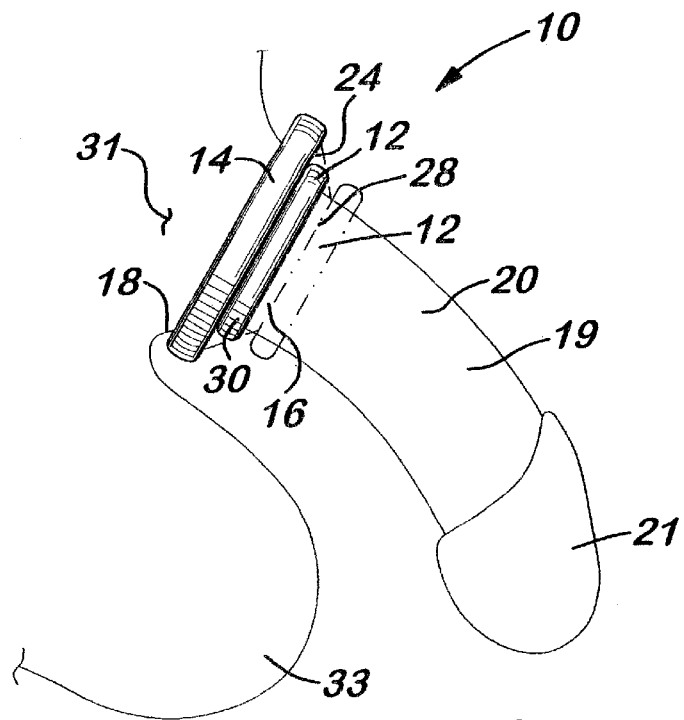
FIG. 4 is a side view of the erection stabilizer mounted on the base of the penis prior to sexual intercourse. In this drawing, the smaller concentric inner ring is shown disposed next to the larger outer ring. Also shown in dotted lines is the inner ring unrolled from a portion of the sheath. The inner ring is positioned a short distance from the outer ring with both rings received around the circumference of the base of penis.

In FIG. 4, a side view of the erection stabilizer 10 is shown mounted on the base 18 of the penis 20 prior to sexual intercourse. In this drawing, the smaller inner ring 12 is shown disposed beside to the larger outer ring 14.

In this drawing and in dotted lines is the inner ring 12 unrolled from a portion of the sheath 16. The inner ring 12 is positioned a short distance from the outer ring 14 with both rings received around the circumference of penis. When it is desired to have less pressure around the base 18 of the penis 20, the stabilizer 10 can be unrolled along a portion of a penis shaft 19. In this manner, the combination of the two rings being spread apart at the base 18 of the penis 20 and along the penis shaft 19 will provide less compression around the circumference of the penis. In this view, a scrotum 33 is shown disposed below the penis 20.

Figure 5:
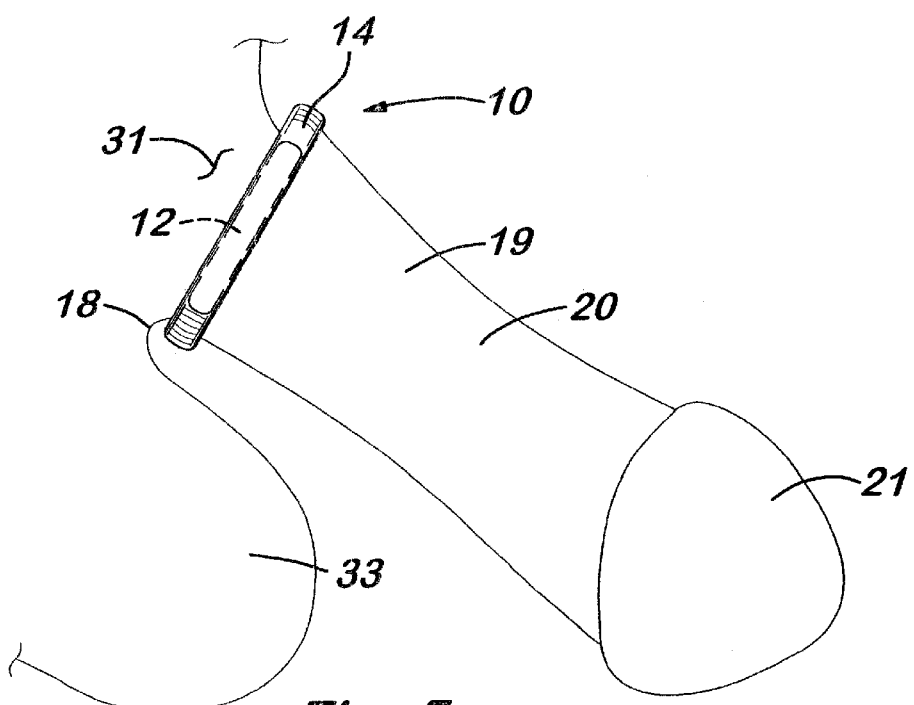
FIG. 5 is another side view of the erection stabilizer mounted on the base of the penis. The penis is shown beginning to be filled with a blood supply and an erection started. In this example, the inner circumference of the outer ring has been placed on the outer circumference of the inner ring for trapping the outflow of blood from the penis. In this manner, the erection stabilizer provides the necessary pressure to contain the blood supply in the penis, thus helping insure a natural and hard erection and creating a necessary hydraulic blood force therein.

In FIG. 5, another side view of the erection stabilizer 10 is shown mounted on the base 18 of the penis 20. The penis 20 is shown beginning to be filled with a blood supply and an enlarged erection started. Note, a head 21 of the penis 20 begins to swell first as more blood enters the penis. In this example, the inner circumference 24 of the outer ring 14 has been placed around the outer circumference 30 of the inner ring 12. The combination of the outer ring 14 placed over the inner ring 12 provides for added pressure to the base 18 of the penis 20. In this manner, the erection stabilizer 10 provides the necessary pressure to contain the blood supply in the penis 20, thus helping insure a natural and harder erection. In this drawing, a portion of the head of the penis 20 can be seen disposed below the scrotum 33.

Figure 6:
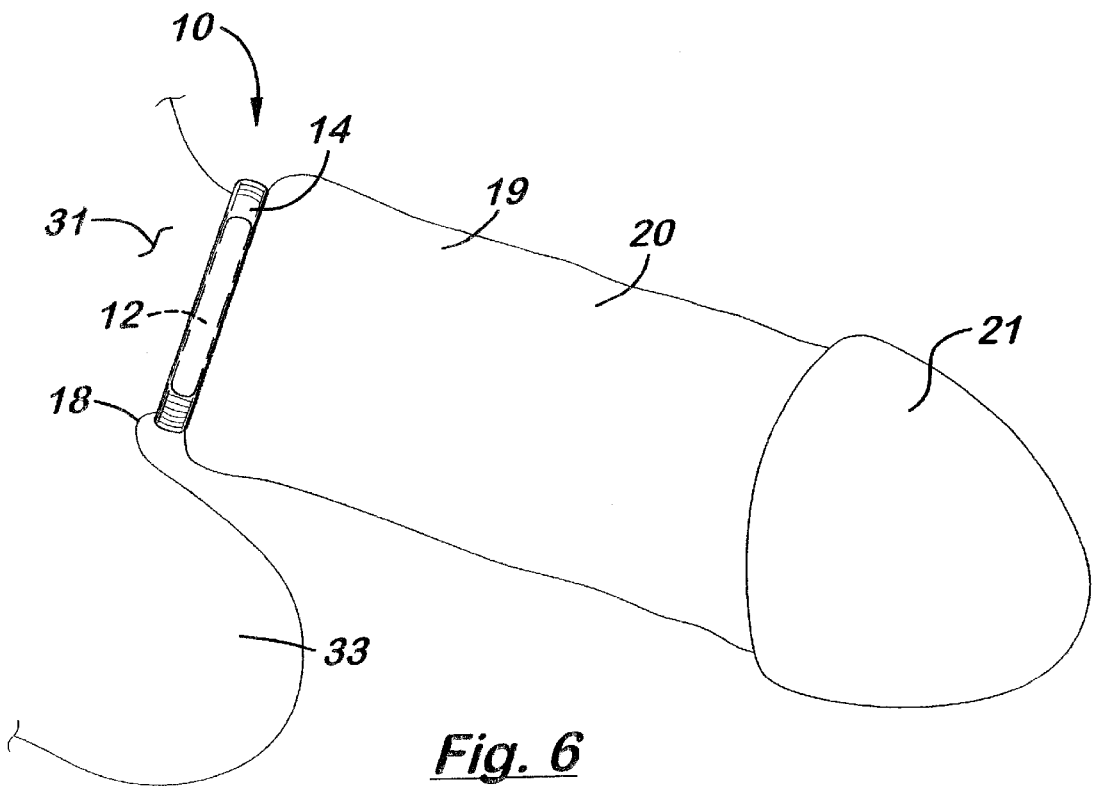
FIG. 6 is still another side view of the erection stabilizer mounted on the base of the penis. In this drawing, the penis is beginning to be completely filled with a blood supply for obtaining and maintaining a full and hard erection.

In FIG. 6, still another side view of the erection stabilizer 10 is shown mounted on the base 18 of the penis 20. In this drawing, the penis 20 has greatly enlarged and is beginning to be completely filled with a blood supply for obtaining a full and hard erection. At this time, the scrotum 33 has begun to shrink in size as the penis 20 is enlarged.

Figure 7:
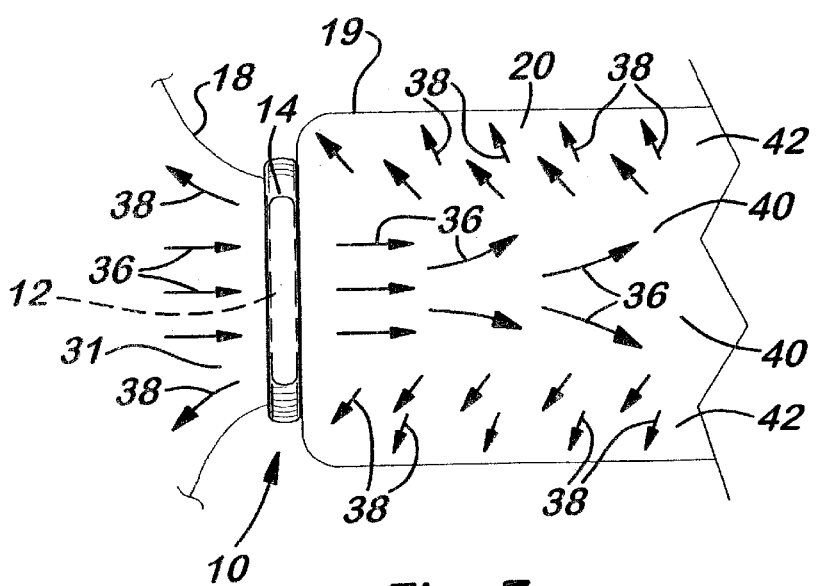
FIG. 7 is a side view of the erection stabilizer received around the base of the penis. only a portion of the penis is shown in this drawing. Arrows are shown to illustrate a flow of a blood supply into the penis for provide an erection. Also, additional arrows are shown illustrating how the erection stabilizer traps the blood supply inside the penis for providing a prolonged natural erection.

In FIG. 7, a side view of the erection stabilizer 10 is shown received around the base 18 of the penis 20. Only a portion of the penis is shown in this drawing. Arrows 36 are shown to illustrate a flow of blood supply into the penis 20 for providing an erection. The arrows 36 flow through a first chamber or a blood in-flow chamber 40. Also, additional arrows 38 are shown illustrating how the erection stabilizer 10 traps the blood supply inside the penis for providing a prolonged erection. The arrows 38 are shown in a second chamber or a blocked blood out-flow chamber 42.

As mentioned above, YES helps create biohematohydraulics or BHH. Biohematohydraulics can be better understood with an explanation of a principal known as Pascal's Law. This law enunciates pressure exerted in a hydraulic system. The effect is demonstrated by a hydraulic press where pressure exerted on a first piston produces an equal increase in pressure on a second piston in the same system. If the second piston has an area ten times that of the first, the force on the second is ten times greater, though the pressure is the same as that on the first piston.

Biologically speaking, biohematohydraulics works as follows. In the same system, like a male body, a heart is pumping and creating pressure inside the arterial walls of a blood artery or capillary carrying blood from the heart. During sexual arousal, sexy signals from the brain stimulate the release of a chemical, cyclic GMP, that cause muscles in the spongy erectile tissue to relax and the arteries to expand inside the penis causing a larger hydraulic piston in the same system. A second piston is the penis shaft where it is being engorged with blood filling the penis erectile tissue.

The outer ring 14 on the base of the penis 20 creates an effective circumference of the penis shaft accomplishing the required restriction of venous blood back-flow into the torso 31. This back-flow is shown as arrows 38 in the back-flow chamber 42. At the same time, the inner ring 12 stretches some allowing the in-flow of blood to flow unrestricted to the penis 20 and allowing passage of urine and semen to flow through the urethra during appropriate moments. This in-flow is shown as arrows 36 in the in-flow chamber 40.

With YES in place, as shown in FIG. 6, a bloodlock in the penis is provided during heightened sexual thinking and activity. When the penis is completely congested with a blood supply, the penis is hard, fully erect, bigger in length and diameter and for a longer period of time. Also, with the head of the penis engorged with blood, the nerves in this area are more sensitive along with the entire penis being more sensitive. Also, during a full erection, there is no more blood pressure inside the penis as in the blood vessels carrying blood inside the torso. However, depending on the size of the penis and the size of the same system's body blood vessels is a ratio of hydraulic force created by biohematohydraulics.

A full erection occurs only after the veins that normally drain blood away from the penis have been squeezed shut. For impotent men, the penis erectile tissue does not expand far enough to plug the back-flow veins due to a shortage of cyclic GMP. Blood flows out the penis as fast as it flows in and the erection falters if not totally fails. YES solves this dilemma. Essentially, YES is a body blood liquid hydraulic pressure bloodlock for generating biohematohydraulics. Fundamentally, YES temporarily traps blood in the penis creating a hydraulic blood force which is generated according to Pascal's Law.

While the invention has been shown, described and illustrated in detail with reference to the preferred embodiments and modifications thereof, it should be understood by those skilled in the art that equivalent changes in form and detail may be made therein without departing from the true spirit and scope of the invention as claimed, except as precluded by the prior art.

The embodiments of the invention for which an exclusive privilege and property right is claimed are defined as follows:

1. A penis erection stabilizer adapted for mounting on a base of a male penis next to a male torso, the erection stabilizer comprising:

a stretchable elastic outer ring, said outer ring adapted for applying sufficient pressure around the circumference of the base of the penis to restrict venous blood back-flow into the torso during a penis erection and allowing the in-flow of blood to flow unrestricted to the penis;

a smaller stretchable elastic inner ring, said inner ring also adapted for applying additional pressure around the circumference of the base of the penis to restrict venous blood back-flow into the torso for creating and maintaining a penis erection and allowing the in-flow of blood to flow unrestricted to the penis; and a sheath, an end portion of said sheath connected to said outer ring, an opposite end portion of said sheath connected to said inner ring.

2. The erection stabilizer as described in claim 1 wherein the end portion of said sheath is connected to an inner circumference of said outer ring, the opposite end portion of said sheath is connected to an inner circumference of said inner ring.

3. The erection stabilizer as described in claim 2 wherein the end portion of said sheath is rolled onto said outer ring, the opposite end portion of said sheath is rolled onto said inner ring.

4. A penis erection stabilizer adapted for mounting on a base of a male penis next a male torso, the erection stabilizer comprising:

a stretchable elastic outer ring, said outer ring adapted for applying sufficient pressure around the circumference of the base of the penis to restrict venous blood back-flow into the torso for creating and maintaining a penis erection and allowing the in-flow of blood to flow unrestricted to the penis;

a smaller stretchable elastic inner ring, said inner ring also adapted for applying additional pressure around the circumference of the base of the penis to restrict venous blood back-flow into the torso for creating and maintaining a penis erection and allowing the in-flow of blood; and a sheath, an end portion of said sheath being rolled onto said outer ring, an opposite end portion of said sheath being rolled onto said inner ring.

5. The erection stabilizer as described in claim 4 wherein the end portion of said sheath is connected to an inner circumference of said outer ring and the opposite end portion of said sheath is connected to an inner circumference of said inner ring.

6. The erection stabilizer as described in claim 4 wherein an outer circumference of said inner ring is received inside and next to an inner circumference of said outer ring.

7. The erection stabilizer as described in claim 4 wherein said inner ring, when unrolled from the opposite end portion of said sheath, is disposed next to one side of said outer ring.

8. A penis erection stabilizer adapted for mounting on a base of a male penis next to a male torso, the erection stabilizer comprising:

a stretchable elastic outer ring, said outer ring adapted for applying sufficient pressure around the circumference of the base of the penis to restrict venous blood back-flow into the torso for creating and maintaining a penis erection and allowing the in-flow of blood to flow unrestricted to the penis;

a smaller stretchable elastic inner ring, said inner ring also adapted for applying additional pressure around the circumference of the base of the penis to restrict venous blood back-flow into the torso during a penis erection and allowing the in-flow of blood to flow unrestricted to the penis, said inner ring having an outer circumference received inside and next to an inner circumference of said outer ring; and a sheath, an end portion of said sheath connected to said outer ring, an opposite end portion of said sheath connected to said inner ring.

9. The erection stabilizer as described in claim 8 wherein the end portion of said sheath is connected to the inner circumference of said outer ring and the opposite end portion of said sheath is connected to an inner circumference of said inner ring.

10. The erection stabilizer as described in claim 8 wherein the end portion of said sheath is rolled onto said outer ring, the opposite end portion of said sheath is rolled onto said inner ring.

* * * * *